(12) United States Patent
Park et al.

(10) Patent No.: US 8,399,223 B2
(45) Date of Patent: Mar. 19, 2013

(54) COMPOSITION CONTAINING ARAZYME FOR THE PREVENTION AND TREATMENT OF CANCER

(75) Inventors: Ho-Yong Park, Daejeon (KR); Kwang-Hee Son, Daejeon (KR); Dong-Ha Shin, Daejeon (KR); Kyu-Shik Jeong, Daegu (KR)

(73) Assignee: Inssect Biotech Co., Ltd., Daejeon (KR)

( * ) Notice: Subject to any disclaimer, the term of this patent is extended or adjusted under 35 U.S.C. 154(b) by 0 days.

(21) Appl. No.: 13/225,317

(22) Filed: Sep. 2, 2011

(65) Prior Publication Data

US 2012/0003204 A1 Jan. 5, 2012

Related U.S. Application Data

(62) Division of application No. 12/521,676, filed as application No. PCT/KR2007/006938 on Dec. 28, 2007, now abandoned.

(30) Foreign Application Priority Data

Dec. 28, 2006 (KR) .................. 10-2006-0136707
Mar. 29, 2007 (KR) .................. 10-2007-0030856

(51) Int. Cl.
*A61K 38/48* (2006.01)

(52) U.S. Cl. ................... 435/94; 435/7.1; 435/252

(58) Field of Classification Search ............... None
See application file for complete search history.

(56) References Cited

FOREIGN PATENT DOCUMENTS

| KR | 10-1998-69206 A | 10/1998 |
|---|---|---|
| KR | 10-2001-112928 A | 12/2001 |
| WO | WO 01/57222 | 8/2001 |

OTHER PUBLICATIONS

Bersanetti, et al., Characterization of arazyme, an exocellular metalloprotease isolated from Serratia proteamaculans culture medium, Enzyme and Microbial Technology, 2005, 37(6):574-581.
Oster Sessuib Abstracts, Bio International Convention, Jun. 17-20, 2008.
Park, et al., Hepatoprotective effect of Arazyme on CCl4-induced acute hepatic injury in SMP30 knock-out mice, Toxicology, 2008, 246(2-3):132-142.
International Search Report from corresponding PCT International Application No. PCT/KR2007/006938.
Wells, Biochemistry, vol. 29, pp. 8509-8717, 1990.

*Primary Examiner* — Hope Robinson
(74) *Attorney, Agent, or Firm* — Lucas & Mercanti, LLP

(57) ABSTRACT

The invention provides a method for treating lung cancer or breast cancer wherein the method comprises administering a pharmaceutically effective dose of arazyme enzyme to a subject with lung cancer or breast cancer. The arazyme enzyme is either a protein comprising the amino acid sequence of SEQ ID NO: 1; and/or a protein encoded by DNA comprising the coding region of the nucleotide sequence of SEQ ID NO: 2.

13 Claims, 11 Drawing Sheets

COMPOSITION CONTAINING ARAZYME FOR THE PREVENTION AND TREATMENT OF CANCER

CROSS-REFERENCE TO RELATED APPLICATIONS

This application is a divisional application of U.S. patent application Ser. No. 12/521,676, filed Jun. 29, 2009 which is a 371 of PCT/KR2007/006938 filed Dec. 28, 2007, which claims the benefit of Korean Patent Application Nos. 10-2006-0136707 filed Dec. 28, 2006 and 10-2007-0030856 filed Mar. 29, 2007, the contents of each of which are all hereby incorporated by reference in their entirety.

TECHNICAL FIELD

The present invention relates to a composition for the prevention and treatment of cancer which comprises arazyme as an active ingredient, more precisely a composition for the prevention and treatment of cancer comprising arazyme that is produced by *Aranicola proteolyticus*.

BACKGROUND ART

A tumor is developed by uncontrollable disordered abnormal cell proliferation. If this tumor shows a destructive growth, invasiveness and metastasis, it is regarded as a malignant cancer. Invasiveness is a character to infiltrate or destroy surrounding tissues, and in particular, a basal layer forming a boundary of tissues is destroyed by the character, resulting in the local spread and sometimes inflow of a tumor through circulatory system. Metastasis means the spread of tumor cells from the original birthplace to other areas through lymphatic or blood vessels. In a broad sense, metastasis also means the direct extension of tumor cells through serous body cavity or other space.

Cancer is caused not only by hereditary factors but also by acquired environmental factors. And advanced countries have higher cancer development rate. The reasons might be the increase of the amounts of pesticides and insecticides used and remaining in foods; the increase of consumption of processed foods containing food preservatives, antiseptics and coloring agents; the increase of water, soil and air pollution; the increase of stress in modern people; the decrease of activity; and obesity resulted from bountiful dietary life (Kim H J, et al., *Liv Sci of Tj Univ.* 3:99-130, 1997; Jacobs M M, *Nutr Tod,* 28(3):19-23, 1993).

Angiogenesis is essential for the growth and metastasis of tumor (Folkman J, *J Natl Cancer Inst,* 82:4-6, 1990). Angiogenesis plays a role in providing nutrition and oxygen to the growing tumor and also enables permeation and metastasis of tumor cells from primary lesion through blood vessel wall to remote organs (Kim K J, et al., *Nature,* 362:841-844, 1993).

As of today, surgical operation, radiotherapy and chemotherapy have been used for the treatment of cancer singly or jointly. The surgical operation is a way to remove diseased tissues. Thus, tumors in specific regions such as breast, colon and skin can be effectively removed by the surgical operation. However, a tumor in vertebra or dispersive tumor like leukemia cannot be properly treated by the surgical operation.

Chemotherapy blocks cell replication or metabolism, and has been used for the treatment of breast cancer, lung cancer and testicular cancer. Though, patients with cancers who have been treated by chemotherapy have seriously suffered from the side effects of systemic chemotherapy. Motion sickness and vomiting are common but serious examples of all. The side effects of chemotherapy can even affect the life of a patient since they might drop the adaptability of a patient rapidly. Besides, DLT (Dose Limiting Toxicity) is also one of major side effects of chemotherapy, which draws a careful attention in the administration of a medicine. Mucositis is an example of DLT against anticancer agents such as 5-fluorouracil which is an antimetabolic cytotoxic agent, and methotrexate, and anticancer antibiotics like doxorubicin. If a patient suffers seriously from such side effects of chemotherapy, he or she should be hospitalized and given an anodyne for reducing pain. So, side effects of chemotherapy and radiotherapy are the biggest problem for the treatment of cancer patients. The conventional anticancer agents kill not only tumor cells but also normal cells. Therefore, recent studies have been focused on the development of a novel anticancer agent that can kill tumor cells only, leaving normal cells untouched.

The present inventors tried to develop a novel protease. As a result, the inventors separated the novel microorganism *Aranicola proteolyticus* HY-3 (Accession No: KCTC 0268BP; WO 01/57222) from *Nephila clavata*. And arazyme, a novel protease, was isolated from the strain. Arazyme showed high enzyme activity at low temperature and at high salt concentration; particularly it exhibited the highest activity at human body temperature 37° C. and stable enzyme activity in wide range of pH. So, the inventors identified the gene of this promising novel protease (WO 01/57222).

The present inventors investigated the effect of arazyme originated from *Aranicola proteolyticus*. As a result, the inventors found out that arazyme increases weight but inhibits tumor cell growth in nude mice transplanted with human lung adenocarcinoma cell line (A549), reduces the expressions of MMP-9, NF-κB and PCNA, reduces the expressions of p21, PCNA (Proliferating Cell Nuclear Antigen), VEGF (Vascular Endothelial Growth Factor), BCl2 (B-cell CLL/lymphoma 2), p-p38, PKC (Protein Kinase C) and MMP-1 (Matrix MetalloProteinase-1) but increases the expression of catalase in human breast cancer cell line (MDA-MB-231). Based on this founding, the present inventors completed this invention by confirming that arazyme can be effectively used for a composition for the prevention and treatment of cancer.

DISCLOSURE

Technical Problem

It is an object of the present invention to provide a composition for the prevention and treatment of cancer comprising arazyme produced by *Aranicola proteolycius*, and a method for the prevention and treatment of cancer using the same.

Technical Solution

To achieve the above object, the present invention provides a pharmaceutical composition for the prevention and treatment of cancer comprising arazyme as an active ingredient.

The present invention also provides health food for the prevention of cancer comprising *Aranicola proteolycius* culture medium or arazyme separated therefrom as an active ingredient.

The present invention further provides a treatment method of cancer including the step of administering the pharmaceutically effective dose of arazyme to a target subject with cancer.

The present invention also provides a prevention method of cancer including the step of administering the pharmaceutically effective dose of arazyme to a target subject with cancer.

In addition, the present invention provides a use of arazyme for the production of a preventive and therapeutic agent of cancer.

Advantageous Effect

Arazyme of the present invention produced by *Aranicola proteolyticus* reduces the expressions of MMP-9, NF-κB, p21, PCNA (Proliferating Cell Nuclear Antigen), VEGF (Vascular Endothelial Growth Factor), BCl2 (B-cell CLL/lymphoma 2), p-p38, PKC (Protein Kinase C) and MMP-1 (Matrix MetalloProteinase-1) which are involved in the growth, differentiation, proliferation and metastasis of tumor cells, but increases the expression of catalase playing a role in inhibiting tumor development.

DESCRIPTION OF DRAWINGS

The application of the preferred embodiments of the present invention is best understood with reference to the accompanying drawings, wherein.

BEST MODE

Figure 1:
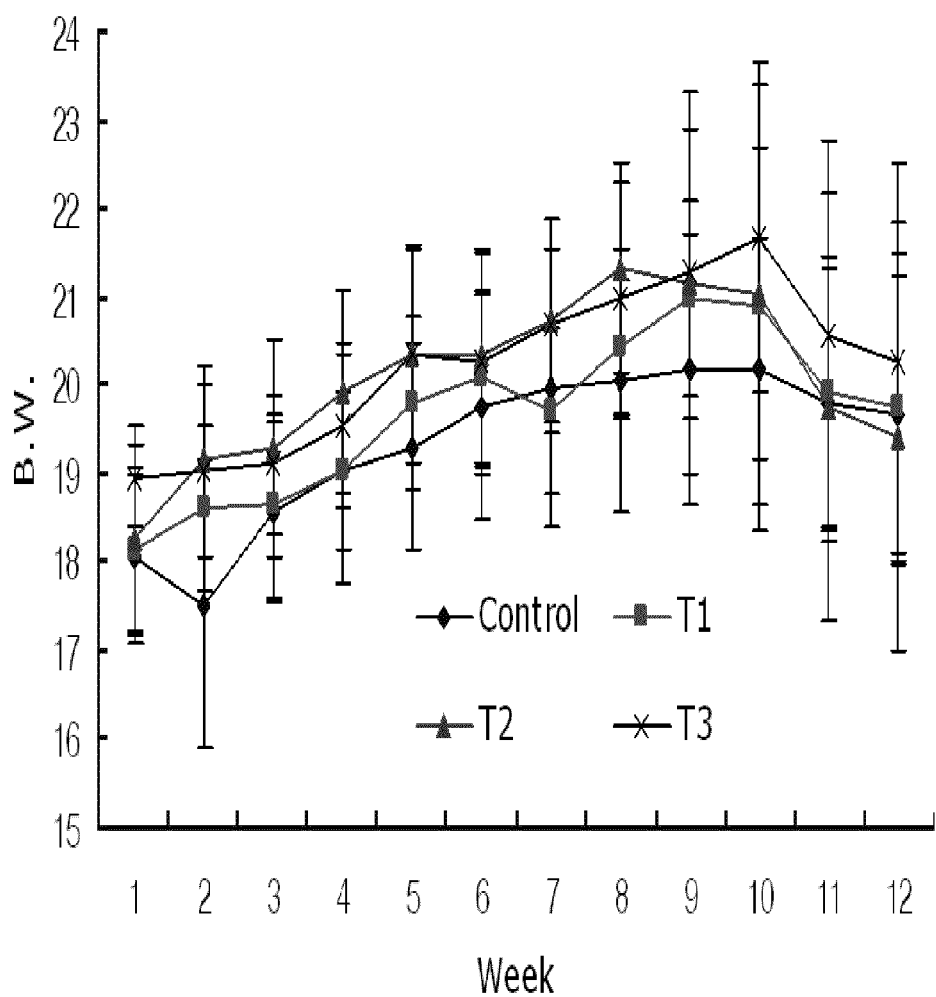
FIG. 1 is a graph showing the weight changes observed after administering arazyme to the nude mice transplanted with human lung adenocarcinoma cell line A549:
Control: orally administered with 0 mg/kg of arazyme;
T1: orally administered with 150 mg/kg of arazyme;
T2: orally administered with 300 mg/kg of arazyme; and
T3: orally administered with 600 mg/kg of arazyme.

Hereinafter, the present invention is described in detail.

Arazyme of the present invention can be prepared by the method comprising the following steps:

1) obtaining culture solution by culturing *Aranicola proteolycius*;

2) obtaining supernatant by filtering the above culture solution; and 3) purifying arazyme from the supernatant by using resin.

In this method, the microorganism that produces arazyme is preferably *Aranicola proteolycius*, and particularly *Aranicola proteolycius* HY-3 deposited at KCTC (Korean Collection for Type Cultures) of KRIBB (Korea Research Institute of Bioscience and Biotechnology) on Jul. 29, 1996 (Accession No: KCTC 0268BP) is more preferred, but not always limited thereto. *Aranicola proteolycius* HY-3 is an aerobic Gram-negative bacterium that is separated from the intestine of *Nephila clavata*, 0.5~0.8 mm in size, in round shape, has mobility, and is positive to catalase but negative to oxidase (WO 01/57222).

In this invention, arazyme obtained from the above is preferably used, and arazyme obtained by the following method is more preferred. Particularly, basic materials for the culture of *Aranicola proteolycius* is preferably in medicine grade, which favors purification with ease and giving a high purity product. After the culture, ammonium sulfate precipitation (or acetone precipitation) is performed, followed by centrifugation and filtering to recover arazyme. Most of other proteins produced in the microorganism have different precipitation concentration from arazyme. After recovering arazyme, the first purification is performed by membrane filter to eliminate impurities and at last final purification is performed using ultra filtration system to obtain pure arazyme. The obtained high concentrated arazyme solution is freeze-dried, resulting in arazyme powder.

Arazyme of the present invention can be produced by the following method:

1) cloning DNA of nucleotide sequence containing the coding region of arazyme into an expression vector;
2) introducing the expression vector of step 1) into host cells;
3) selecting host cells transformed in step 2); and
4) obtaining arazyme expressed from the host cells selected in step 3).

In this method, the nucleotide sequence containing the coding region of arazyme of step 1) is preferably DNA represented by SEQ ID NO: 2 or DNA hybridized with the DNA containing the nucleotide sequence represented by SEQ ID NO: 2 under strict condition. The strict condition is determined during washing after hybridization. For example, the strict condition indicates washing at room temperature with 6×SSC, 0.5% SDS for 15 minutes, washing at 45° C. with 2×SSC, 0.5% SDS for 30 minutes and washing at 50° C. with 0.2×SSC, 0.5% SDS for 30 minutes and repeating the washing twice. More preferably, the strict condition indicates that washing is performed at higher temperature. Particularly, washing is performed by the same conditions as the above except that the last two washings are performed at 60° C. with 0.1×SSC, 0.5% SDS for 30 minutes or at 65° C. with 0.1× SSC, 0.1% SDS for 30 minutes. Such strict conditions can be determined or regulated by those in the art. The expression vector herein is preferably the conventional. Gram negative bacteria or Gram positive bacteria well-known to those in the art. A commercial vector also can be used and it is more preferred for the vector to include a drug resistant gene for better screening. Any vector can be used as long as it does not affect arazyme gene.

In the above method, the host cell of step 2) can be selected from the group consisting of bacteria such as *E. coli* and *Bacillus subtilis* and yeasts such as *Saccharomyces cerevisiae, Candia* and *Phicia*, but not always limited thereto.

In the above method, the selection of the host cell successfully transformed in step 3) is performed by screening using the drug resistant gene introduced in the vector independently or in parallel with screening using Southern blotting or PCR.

In the above method, arazyme in step 4) can be obtained by any protein purification method. For example, the protein purification is exemplified by column chromatography, filtration, ultra filtration, salting out, solvent precipitation, solvent extraction, distillation, immuno-precipitation, SDS-polyacryl amide gel electrophoresis, isoelectric point electrophoresis, dialysis or recrystallization, but not always limited thereto. Arazyme encoded by DNA can be obtained by the conventional protein expression systems well-known to those in the art. Arazyme is also obtained from cell culture by the processes of recovering and purifying.

Arazyme of the present invention is preferably selected from the following proteins, but not always limited thereto:

(a) the protein containing the amino acid sequence represented by SEQ ID NO: 1;
(b) the protein encoded by the DNA containing the coding region of the nucleotide sequence represented by SEQ ID NO: 2;
(c) the protein composed of amino acid sequence mutated from the amino acid sequence represented by SEQ ID NO: 1 with substitution, deletion, insertion and/or addition of one or more amino acids therein and functionally equal to the protein containing the amino acid sequence represented by SEQ ID NO: 1; and
(d) the protein encoded by the DNA hybridized with the DNA containing the nucleotide sequence represented by SEQ ID NO: 2 under the strict conditions and functionally equal to the protein containing the amino acid sequence represented by SEQ ID NO: 1.

The hybridization under the strict conditions gives DNA having high homology in nucleotide sequence, suggesting that it is very much likely that the isolated protein has the protein functionally equal to arazyme. The nucleotide sequence having high homology indicates the nucleotide sequence having more than 70% homology with the nucleotide sequence represented by SEQ ID NO: 2 preferably more than 80% and more preferably more than 90% and most preferably more than 95% homology with the nucleotide sequence represented by SEQ ID NO: 2. And the amino acid sequence having more than 70% homology with the amino acid sequence represented by SEQ ID NO: 1, preferably more than 80% and more preferably more than 90% and most preferably more than 95% homology with the amino acid sequence represented by SEQ ID NO: 1 can be used. The rate of homology can be determined by the conventional algorithm selected by those in the art. The hybridization can be performed by DNA-DNA hybridization under the strict conditions well-known to those in the art, as mentioned hereinbefore, in relation to washing after hybridization (Hames and Higgins, Eds. (1985) Nucleic Acid Hybridization, IRL Press, U.K.).

The present invention provides a pharmaceutical composition for the prevention and treatment of cancer comprising arazyme as an active ingredient.

The cancer herein can be selected from the group consisting of lung cancer, breast cancer, liver cancer, stomach cancer, colon carcinoma, brain tumor, pancreas cancer, head carcinoma, cervical cancer, uterine cancer, ovarian cancer, rectal cancer, esophageal cancer, small intestine cancer, anal cancer, fallopian tube carcinoma, endometrial carcinoma, cervix carcinoma, vaginal carcinoma, vulvar carcinoma, Hodgkin's disease, prostatic carcinoma, bladder cancer, kidney cancer, ureter cancer, renal cell carcinoma, pelvic carcinoma and CNS (central nervous system) tumor.

To investigate the anticancer effect of arazyme, the present inventors transplanted human lung adenocarcinoma cell line (A549) to nude mice, which were divided into 4 groups: control group (treated with 0 mg/kg of arazyme), T1 (treated with 150 mg/kg of arazyme), T2 (treated with 300 mg/kg of arazyme) and T3 (treated with 600 mg/kg of arazyme). Arazyme was orally administered repeatedly (see Table 1). Arazyme was dissolved in sterilized solution for injection, which was administered orally 6 times per week by using zonde. Weight changes and other general symptoms were observed after the arazyme administration. Tumor development was also observed once a week, and if confirmed, the size would be measured. 12 weeks after the arazyme administration, autopsy was performed. No pathological changes were observed over all the organs by the naked eye and under microscope. Weight gaining was confirmed in T2 and T3, respectively administered with 300 mg/kg and 600 mg/kg of arazyme (see Table 2 and FIG. 1). The size of tumor taken from the nude mice transplanted with human lung adenocarcinoma cell line (A549) was measured and immunohistochemical observation using hematoxylin-eosin staining (H&E staining) was also performed. As a result, arazyme dose-dependent tumor suppressing effect and tumor cell infiltration inhibiting effect were confirmed in T2 (treated with 300 mg/kg of arazyme) and T3 (treated with 600 mg/kg of arazyme) (see FIGS. 2 and 3).

Matrix metalloproteinases (MMPs) is a protease, particularly decomposing extracellular matrix (ECM) (Matrisan L M, *Trends Genet,* 6:121-125, 1990). It is understood that when MMPs increase, tumor infiltration and metastasis increase along with inflammation in various cancers (Stearns M A, et al., *Cancer Res,* 53:878-883, 1993). It is the first step of metastasis to decompose collagen type IV which is the most important structure of the basement membrane of blood vessel, by which infiltration into blood stream becomes possible. The decomposition of collagen type IV is carried out by MMP-9 and MMP-2 among many MMPs (Liotta L A, et al., *Cell,* 64:327-336, 1991). MMP is acknowledged as an important factor necessary for migration of vascular endothelial cells and germination in angiogenesis (Fisher C, et al., *Devel Biol,* 162:499-510, 1994). The activity of MMP is regulated by 1) transcriptional regulation of MMP gene; 2) precursor activity; 3) difference of lipid specificity; and 4) MMP inhibitors such as alpha-macroglobulins and tissue matrix metalloproteinases inhibitor (TIMPs) (Birkedal-Hansen. H, *J periodontol,* 64:474-484, 1993). Growth factors including mitogen-activated protein kinases (MAPKs), cytokines, and tumor promoters are involved in the higher signal transduction mechanism regulating the expression of MMP-9. Among these factors, p38 kinase and extracellular signal-regulated protein kinase (ERK) are activated by inflammatory cytokines or apoptosis related signals and growth factors. The activated MAPKs migrate to nuclei and are reacted with transcription factor binding site around MMP origin to activate various transcription factors to regulate the expressions of lower target proteins. Most cancer cells are transferred from the primary lesion to the secondary lesion by the processes of substrate infiltration, migration from the primary lesion through blood system to the secondary lesion, and generation of the secondary tumor. For cancer cell infiltration process, extracellular substrate is necessarily decomposed by a protease and at this time MMPs play a key role in decompositing the extracellular substrate. Among various MMPs, MMP-2 and MMP-9 are 72 and 92 kDa collagenase respectively which decompose collagen that forms cell basement membrane to accelerate cancer infiltration and metastasis (Himelstein B P, et al., *Invasion Metastasis,* 14:246-258, 1994).

The present inventors performed experiments using nude mice transplanted with human lung adenocarcinoma cell line (A549) and the result confirmed that the MMP-9 expression was reduced by the administration of arazyme (see FIGS. 4 and 5), indicating that arazyme has anticancer effect.

Nuclear transcription factor-κB (NF-κB) is the transcription factor inducer that is activated by various environmental stimuli (Baeuerle, P A and Baichwal, V R, *Adv Immunol* 65:111-137, 1997; Auphan, N, et al., *Science,* 270:286-290, 1995). The dormant NF-κB is bound to I-κB, the suppresser protein, in cytoplasm. Various NF-κB activators such as tumor necrosis factor, IL-1, lipopolysaccharides and UV (ultraviolet) induce degradation of I-κB by phosphorylation and ubiquitination. By this process, NF-κB is separated from I-κB and then transferred into nuclei to bind to NF-κB-binding site on the promoter region of a target gene to stimulate the target gene expression (Baldwin, A S, *Annu Rev Immunol,* 14:649-683, 1996; Huxford T, et al., *Cell,* 95:759-770, 1998). NF-κB is also an important factor involved in drug refractoriness. It plays an important role in cytokine synthesis. When it is activated as a transcription factor inducing expressions of various genes involved in immune response or inflammation, it migrates to nucleus and increases the expression of inflammation related gene.

The present inventors performed experiments using nude mice transplanted with human lung adenocarcinoma cell line (A549) and the result confirmed that the NF-κB expression was reduced by the administration of arazyme (see FIGS. 6 and 7), indicating that arazyme has tumor growth inhibiting effect.

PCNA is not found in G0 phase of the cell cycle, but begins to increase in G1 phase, demonstrates the highest level in S phase and decreases in G2 phase. PCNA is a coprotein of 36 kDA sized intracellular DNA polymerase delta, which is necessary for intracellular DNA synthesis and cell proliferation (Miyagawa S, et al., *J Invest Dematol,* 93:678-681, 1989). In general, histoimmunofluorescence method with PCNA has been an important index telling what region and how many are involved in tumor growth. The expression of PCNA is allegedly associated with the proliferation of keratinocytes, gliosis, stained skin lesion, and histopathological grade of non small cell lung carcinoma PCNA (Underhill C, *J Cell Sci,* 103:293-298, 1992).

The present inventors performed experiments using nude mice transplanted with human lung adenocarcinoma cell line (A549) and the result confirmed that the PCNA expression was reduced by the administration of arazyme (see FIGS. 8 and 9), suggesting that arazyme has tumor growth inhibiting effect.

To examine the anticancer effect of arazyme, the present inventors treated human breast cancer cells (MDA-MB-231) with arazyme (60 μg/ml, followed by observation on the levels the proteins involved in tumor cell growth, differentiation, proliferation and metastasis. The human breast cancer cell line (MDA-MB-231), among all the human breast cancer cell lines, is the malignant cancer cell line that does not have estrogen receptor (Liu Y, et. al., *Biochem Biophys Res Commun.* 2006; 344: 1263-1270; Wyatt C A, et. al., *Cancer Res.* 2005; 65: 11101-11108). The CDK (Cyclin Dependent Kinase) inhibitor p21 is the protein involved in tumor cell growth and differentiation by regulating the expressions of cyclin A, D, and E (Westhof G, et. al., *Tumour Biol.* 2006, 27: 252-60; Rayala S K, et. al., *Cancer Res.* 2006, 66: 5985-5988).

The present inventors confirmed that the p21 expression was inhibited by arazyme in human breast cancer cells.

p38 involved in intracellular signaling pathway of MAPK (Mitogen-Activated Protein Kinase) is the protein expressed by stress-related mechanism, which is also known to stimulate breast cancer cell growth (Lowe L C, et. al., *Biochem Biophys Res Commun.* 2005, 329: 772-779; Pettersson F, et. al., *Oncogene.* 2004, 23: 7053-7066).

The present inventors confirmed that the p38 expression was inhibited by arazyme in human breast cancer cells.

Protein kinase is involved in cell growth/differentiation/gene expression and PKC (Protein Kinase C) is up-regulated in malignant tumor (Pettersson F, et. al., *Oncogene.* 2004, 23: 7053-7066; Ribeiro-Silva A, et. al., *Histol Histopathol.* 2006, 21: 373-382; Tan M, et. al., *Oncogene.* 2006, 25: 3286-3295).

The present inventors confirmed that the PKC (Protein Kinase C) was down-regulated by arazyme in breast cancer cells, suggesting that arazyme had the inhibitory effect on the tumor cell proliferation.

The present inventors further confirmed that the expressions of PCNA (Proliferating Cell Nuclear Antigen) (Kumaraguruparan R, et. al., *Res Vet Sci.* 2006, 81: 218-224; Lyzogubov V, et. al., *Exp Oncol.* 2005, 27: 141-144), the marker protein of tumor cell proliferation; VEGF (Vascular Endothelial Growth Factor) (Kou B, et. al., *Oncol Res.* 2005, 15: 239-247), the marker protein of angiogenesis; MMP-1 (Matrix MetalloProteinase-1) (Zhang C, et. al., *Mol. Ther.* 2006, 13: 947-955; Wyatt C A, et. al., *Cancer Res.* 2005, 65: 11101-11108) involved in tumor infiltration and metastasis; and BCl2 (B-cell CLL/lymphoma 2) (Kumaraguruparan R, et. al., *Res Vet Sci.* 2006, 81: 218-224; Emi M, et. al., *Breast Cancer Res.* 2005, 7: R940-R952; Sirvent J J, et. al., *Histol Histopathol.* 2004, 19: 759-770) were all inhibited significantly by arazyme in human breast cancer cells, compared with non-treated control group.

In tumor development, ROS (Reactive Oxygen Species) generated by tumor cells is a key factor for the proliferation of tumor cells (Tas F, et. al., *Med Oncol.* 2005, 22, 11-15). Catalase plays a role in eliminating ROS like hydrogen peroxide, suggesting that catalase has inhibiting effect on tumor development (Tas F, et. al., *Med Oncol.* 2005, 22, 11-15; Ozkan A, et. al., Exp Oncol. 2006, 28: 86-88).

The present inventors observed that the expression of catalase was up-regulated by arazyme in human breast cancer cells. The above results suggest that arazyme not only inhibits the tumor cell growth, proliferation and differentiation but also inhibits MMP and PKC, both involved in metastasis of malignant tumor, so that arazyme has inhibiting effect on metastasis.

The present inventors orally administered arazyme to female Wistar rats to investigate toxicity. As a result, no abnormal signs or pathological symptoms were observed by the naked eye at the concentrations of 0, 1250, and 5000 mg/kg. So, arazyme orally administered in this experiment is evaluated to be a safe substance since its estimated $LD_{50}$ value is much greater than 5,000 mg/kg in rats. Therefore, arazyme of the present invention can be effectively used as a composition for the prevention and treatment of breast cancer.

The composition of the present invention can include, in addition to arazyme, one or more effective ingredients having the same or similar function to arazyme. The composition of the present invention can be administered orally or parenterally and be used in general forms of pharmaceutical formulation. The composition of the present invention can be prepared for oral or parenteral administration by mixing the active ingredient with generally used fillers, extenders, binders, wetting agents, disintegrating agents, diluents such as surfactant, or excipients. Solid formulations for oral administration are tablets, pill, dusting powders and capsules. These solid formulations are prepared by mixing the active ingredient with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerinated gelatin, etc. The composition can further be prepared in suitable forms for each disease or according to ingredients by following the method represented in Remington's Pharmaceutical Science (the newest edition), Mack Publishing Company, Easton Pa.

The composition for the prevention and treatment of cancer of the present invention can be administered orally or parenterally (for example, intravenous, hypodermic, local or peritoneal injection). The effective dosage of the composition can be determined according to weight, age, gender, health condition, diet, administration frequency, administration method, excretion and severity of a disease. The dosage of arazyme is 0.01~5000 mg/kg per day and preferably 0.01~10 mg/kg per day, and administration frequency is once a day or preferably a few times a day.

The present invention also provides a treatment method of cancer including the step of administering the pharmaceutically effective dose of arazyme to a target subject with cancer.

The present invention further provides a prevention method of cancer including the step of administering the pharmaceutically effective dose of arazyme to a target subject with cancer.

In addition, the present invention provides a use of arazyme for the production of a preventive and therapeutic agent of cancer.

As explained hereinbefore, arazyme was administered to nude mice transplanted with human lung adenocarcinoma cell line (A549) and to breast cancer cells. As a result, arazyme inhibited the expressions of MMP-1, MMP-9, NF-κB, p21, PCNA, VEGF, BCl2, p-p38 and PKC which are involved in the tumor cell growth, proliferation and differentiation, but stimulated the expression of catalase that inhibits tumor generation. Therefore, arazyme of the invention can be effectively used for the development of methods for prevention and treatment of cancer comprising the step of administering arazyme to a target subject with cancer or for the production of a preventive and therapeutic agent of cancer.

The present invention also provides health food for the prevention of cancer comprising *Aranicola proteolycius* culture medium or arazyme separated therefrom as an active ingredient.

The *Aranicola proteolycius* culture medium or arazyme separated from the same of the invention can be used as food additive. In that case, the *Aranicola proteolycius* culture medium or arazyme separated from the same can be added as it is or as mixed with other food components according to the conventional method. Arazyme is obtained by the same manner as described above. The mixing ratio of active ingredients can be regulated according to the purpose of use (prevention, health enhancement or treatment). In general, to produce health food or beverages, the *Aranicola proteolycius* culture medium or arazyme separated from the same is added preferably by 0.01~10 weight part and more preferably by 0.05~1 weight part. However, if long term administration is required for health and hygiene or regulating health condition, the content can be lower than the above but higher content can be accepted as well since arazyme has been proved to be very safe.

The food herein is not limited. For example, the *Aranicola proteolycius* culture medium or arazyme separated from the same can be added to meats, sausages, breads, chocolates, candies, snacks, cookies, pizza, ramyuns, flour products, gums, dairy products including ice cream, soups, beverages, tea, drinks, alcohol drinks and vitamin complex, etc, and in wide sense, almost every food applicable in the production of health food can be included.

The composition for health beverages of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and sugar alcohols such as xilytole, sorbitol and erythritol. Besides, natural sweetening agents such as thaumatin and stevia extract, and synthetic sweetening agents such as saccharin and aspartame can be included as a sweetening agent. The content of the natural carbohydrate is preferably 0.01-0.04 g and more preferably 0.02-0.03 g in 100 ml of the composition.

In addition to the ingredients mentioned above, the *Aranicola proteolycius* culture medium or arazyme separated therefrom of the present invention can include in variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, carbonators which used to be added to soda, etc. The *Aranicola proteolycius* culture medium or arazyme separated therefrom of the present invention can also include natural fruit juice, fruit beverages and/or fruit flesh addable to vegetable beverages. All the mentioned ingredients can be added singly or together. The mixing ratio of those ingredients does not matter in fact, but in general, each can be added by 001-0.1 weight part per 100 weight part of the *Aranicola proteolycius* culture medium or arazyme separated therefrom of the invention.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Arazyme

To prepare arazyme, the active ingredient of the present invention, *Aranicola proteolycius* HY-3 (KCTC 0268BP) was cultured in a culture medium (bacto-trypton 0.5%, yeast extract 0.5%, sodium chloride 0.1%, potassium chloride 0.05%, calcium chloride 0.02%, magnesium sulfate 0.02%) at. 22° C. for 18 hours. The culture solution was filtered by membrane filtration (2 μm filter, Satorius, USA) to separate supernatant from the cells. The supernatant was concentrated by membrane filtration (10 kDa Membrane filter, Pall sept, PALL Corporation, USA). Arazyme of the invention has the characteristics of anion. So, the concentrated solution was purified by ion exchange resin (Sigma USA) using DEAE-cellulose (Sigma, USA) pre-treated with 50 mM tris-HCl buffer (pH 7.6) and gel, filtration exchange resin using Sephadex G-75 (Sigma USA) pre-treated with 20 mM tris-HCl buffer (pH 7.6). The purified enzyme solution was electrophoresed on 10% SDS-PAGE (Sodium dodecyl sulfate-polyacrylamide gel), and band pattern was observed. As a result, arazyme was identified as a monomer not having a subunit and showed the band of approximately 51.5 kDa. The *Aranicola proteolycius* HY-3 (KCTC 0268BP) can be cultured in various commercial media to produce arazyme and the culture solution thereof can be separated and purified by various methods. Arazyme of the present invention has the amino acid sequence represented by SEQ ID NO: 1 and the nucleotide sequence represented by SEQ ID NO: 2.

Example 2

Arrangement of Experimental Mice and Administration 5-week old specific pathogen (SPF) free CAnN.Cg-Foxn1nu/CrljBgi line nude mice (15 g, Orient, Korea) were used in this invention.

The mice were inspected and adapted for 7 days in an animal laboratory. During the adaptation, general symptoms were observed and only healthy animals were selected for the experiment.

The mice were adapted and raised in an animal laboratory equipped with automatic temperature/humidity regulator by which temperature was set at 22±3° C. and the relative humidity was regulated to be 55±10% and light interval was set at 12 hours (light on at 08:00 and light off at 20:00). The environmental conditions were checked regularly (once every three months). From environmental checkup, any environmental changes that might affect the experiment did not detected. During the whole experimental period, the mice were accommodated less than 5 per each polycarbonate cage [240 W×390 L×175 H (mm)]. For individual identification, both skin mark using an oil marker and distinction cards were used. Solid feed for test animals (PMI Nutrition International, 505 North 4th Street Richmond, in 47374, USA) was sterilized by irradiation (13.2 kGy) and provided freely. Tap water was purified by a carbon filter and given by a water bottle freely.

After 1 week of adaptation, human lung adenocarcinoma cells (A549) were transplanted under the left armpits of the mice ($1 \times 10^7$ cells/mouse) to form a tumor. The mice transplanted were divided into 4 groups and each was treated with 0 mg/kg of arazyme (control), 150 mg/kg of arazyme (T1), 300 mg/kg of arazyme (T2), and 600 mg/kg of arazyme (T3) respectively for 12 weeks (Table 1). The treatment was performed by oral-administration using zonde 6 times a week. During the whole experimental period, weight changes and other general symptoms were observed. After 12 weeks, autopsy was performed.

Experimental group composition is shown in Table 1.

TABLE 1

Experimental group composition

| Group | Mark | Xenograft (S.C.) | Oral administration of arazyme |
|---|---|---|---|
| Control | 1-10 | A549 $1 \times 10^7$ cells/mouse | 0 mg/kg |
| T1 | 11-20 | A549 $1 \times 10^7$ cells/mouse | 150 mg/kg |
| T2 | 21-30 | A549 $1 \times 10^7$ cells/mouse | 300 mg/kg |
| T3 | 31-40 | A549 $1 \times 10^7$ cells/mouse | 600 mg/kg |

Example 3

Cell Culture

In the present invention, an estrogen receptor negative human breast cancer cell line MDA-MB-231 (HTB-26) provided from ATCC (American Type Culture Collection, USA) distributed from ATCC was used.

<3-1> Cell Culture Conditions

The human breast cancer cell line (MDA-MB-231) was subcultured every 2-3 days in DMEM supplemented with 10% FBS (fetal bovine serum) and 1% ampicillin in a 37° C. 5% $CO_2$ incubator. Sterilized culture dishes were used for the experiment.

<3-2> Arazyme Treatment

The human breast cancer cell line (MDA-MB-231) was inoculated in a 6-well dish (6×10⁵ cells/well), followed by culture at 37° C. for overnight. The medium was replaced with a starvation medium containing 1% FBS 4 hours before arazyme was treated, resulting in cell cycle arrest. Arazyme was diluted in sterilized injectable solution at the concentration of 60 μg/ml, which was treated to the culture dish. The culture dish was cultured again in a 37° C. incubator for further 34 hours.

Experimental Example 1

Weight Changes by Arazyme Treatment

Human lung carcinoma cell line (A549) was transplanted to the nude mice by the same manner as described in Example 2. Weight was measured once a week to record weight changes and other general symptoms were also investigated.

Through the entire experimental period (12 weeks), weight of the mice treated with arazyme increased, in particular weight changes in the groups treated with 300 mg/kg of arazyme (T2) and 600 mg/kg of arazyme (T3) were significant (Table 2 and FIG. 1).

TABLE 2

| | Mouse weight Weight change (g) | | | |
|---|---|---|---|---|
| Week | Control 10 mice Weight | T1 10 mice Weight | T2 10 mice Weight | T3 10 mice Weight |
| 1 | 18.05 ± 0.95 | 18.15 ± 0.93 | 18.26 ± 1.08 | 18.96 ± 0.57 |
| 2 | 17.52 ± 1.63 | 18.62 ± 0.93 | 19.14 ± 1.07 | 19.03 ± 0.96 |
| 3 | 18.57 ± 1.02 | 18.63 ± 1.06 | 19.30 ± 1.24 | 19.11 ± 0.78 |
| 4 | 19.04 ± 1.29 | 19.03 ± 0.88 | 19.92 ± 1.15 | 19.54 ± 0.93 |
| 5 | 19.30 ± 1.17 | 19.78 ± 0.98 | 20.34 ± 1.23 | 20.33 ± 1.22 |
| 6 | 19.75 ± 1.27 | 20.08 ± 1.00 | 20.33 ± 1.21 | 20.25 ± 1.24 |
| 7 | 19.97 ± 1.58 | 19.72 ± 0.94 | 20.74 ± 1.15 | 20.67 ± 1.20 |
| 8 | 20.05 ± 1.49 | 20.42 ± 0.79 | 21.33 ± 1.18 | 21.00 ± 1.32 |
| 9 | 20.16 ± 1.53 | 21.00 ± 1.10 | 21.17 ± 2.17 | 21.27 ± 1.64 |
| 10 | 20.16 ± 1.50 | 20.92 ± 1.75 | 21.01 ± 2.65 | 21.66 ± 1.75 |
| 11 | 19.78 ± 1.56 | 19.91 ± 1.56 | 19.77 ± 2.42 | 20.58 ± 2.19 |
| 12 | 19.67 ± 1.58 | 19.74 ± 1.77 | 19.41 ± 2.42 | 20.27 ± 2.26 |

Control: orally administered with 0 mg/kg of arazyme;
T1: orally administered with 150 mg/kg of arazyme;
T2: orally administered with 300 mg/kg of arazyme; and
T3: orally administered with 600 mg/kg of arazyme.

Experimental Example 2

Tumor Growth Inhibition by Arazyme Treatment

Human lung carcinoma cell line (A549) was transplanted to the nude mice. From the 5th week, a tumor was observed with the naked eye and since then the tumor size of each mouse had been measured using a caliper once a week for 8 weeks. The volume of the tumor was calculated by measuring major axis and minor axis of the tumor according to the following formula 1.

$$\text{Tumor volume(mm}^3\text{)} = (\text{Major axis} \times \text{Minor axis}^2)/2 \qquad \text{<Formula 1>}$$

Figure 2:
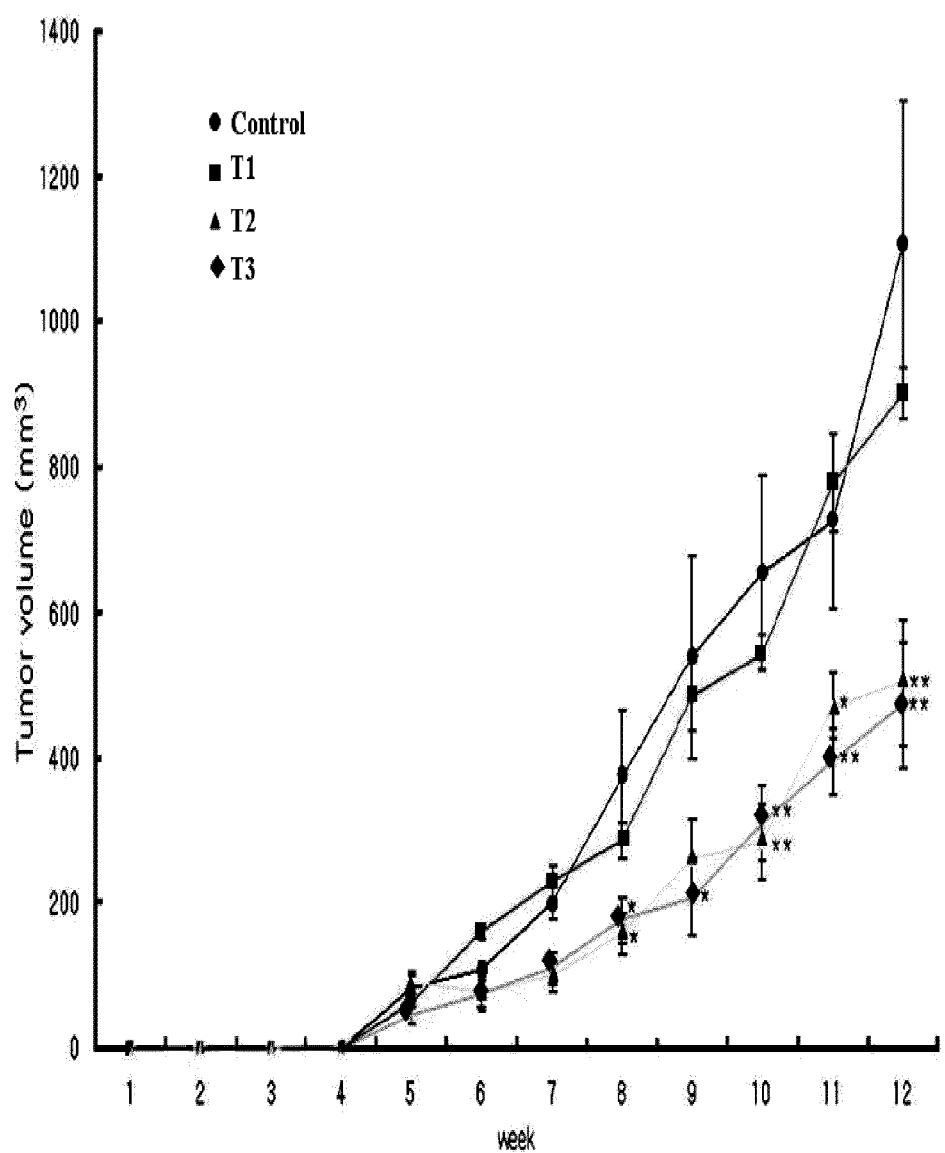
FIG. 2 is a graph showing the tumor size observed after administering arazyme to the nude mice transplanted with human lung adenocarcinoma cell line A549:
Control: orally administered with 0 mg/kg of arazyme;
T1: orally administered with 150 mg/kg of arazyme;
T2: orally administered with 300 mg/kg of arazyme;
T3: orally administered with 600 mg/kg of arazyme.
*: $p<0.05$; and **: $p<0.01$.

As a result, significant decrease of the tumor size was observed in the groups treated with 300 mg/kg of arazyme (T2) and 600 mg/kg of arazyme (T3) through the experimental period, compared with the control (FIG. 2).

Experimental Example 3

Effect of Arazyme on Lung Cancer Tissues

Human lung carcinoma cell line was transplanted to the nude mice. 12 weeks later, the mice were anesthetized with ethyl ether and sacrificed to take out tumors and organs. The tumors were weighed. Heart, liver, lung, pancreas, kidney and spleen were extracted. The tumor and organs were fixed in 10% neutral formalin for 24 hours and processed to tissue treatment with automatic tissue processor. The tumor and organs finished with the tissue process were embedded in paraffin and sectioned by 4 μm in thick. The sections were stained with hematoxylin-eosin and observed under optical microscope.

Figure 3:
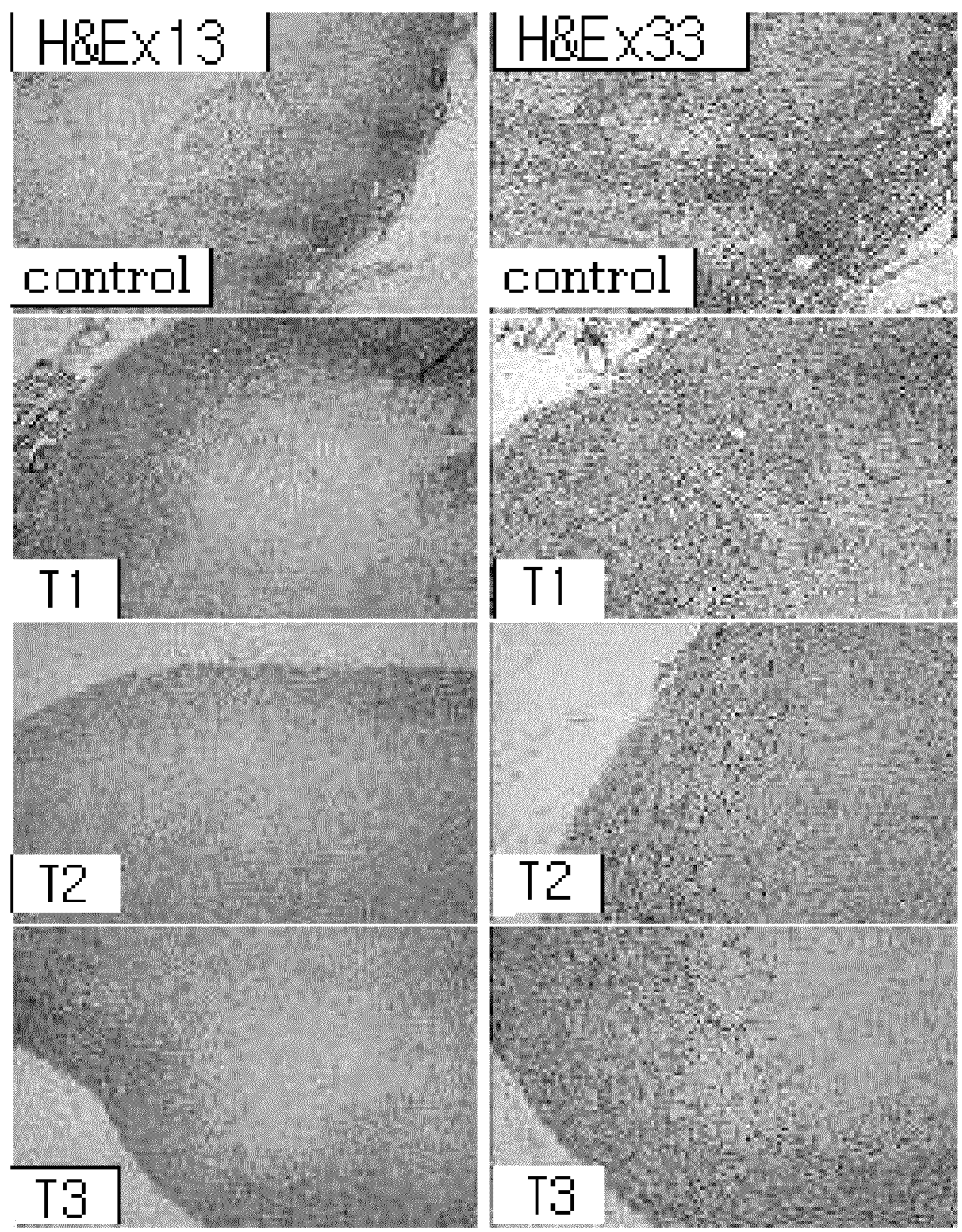
FIG. 3 is a set of photographs (x13 and x33) illustrating the histological changes observed after administering arazyme to the nude mice transplanted with human lung adenocarcinoma cell line A549:
Control: orally administered with 0 mg/kg of arazyme;
T1: orally administered with 150 mg/kg of arazyme;
T2: orally administered with 300 mg/kg of arazyme; and
T3: orally administered with 600 mg/kg of arazyme.

As a result, tumor cell infiltration in the group treated with arazyme was slow, compared with the control (FIG. 3).

Experimental Example 3

Effect of Arazyme on the Expression of MMP-9

For the immunohistological investigation on MMP-9, the paraffin embedded tissues fixed with formalin was sectioned by 4 μm, followed by deparaffination. The sections were treated with 3% $H_2O_2$ for 30 minutes to inhibit the activity of endogenous peroxidase and then washed with 0.01 M phosphate-buffer saline (PBS). The sections were then treated with 0.01 M citrate buffer to increase the expression of tissue antigen, followed by heat treatment with microwave. To inhibit non-specific reaction, the sections were treated with 20 g/ml of proteinase K at 37° C. for 10 minutes and washed with PBS, followed by blocking for 1 hour. The sections were treated with anti-rabbit primary antibody MMP-9 (1:100, Santa Cruz Bio, USA) at 4° C. for overnight and washed with PBS three times for 5 minutes, followed by conjugating with biotin. The biotin-conjugated primary antibody was washed with buffer, to which streptavidin-conjugated HRP (Horse-Rradish Peroxidase) was attached, followed by reaction using Histostantin-plus bulk kit (Zymed Laboratories Inc, USA) at 37° C. for 30 minutes. After washing thoroughly, color development was induced using DAB (3,3-diaminobenzidine tetrahydrochloried, Zymed Laboratories Inc, USA) solution. After washing with distilled water, counter staining was performed with Meyer's hematoxylin (Research genetics, USA), followed by observation under optical microscope.

Figure 4:
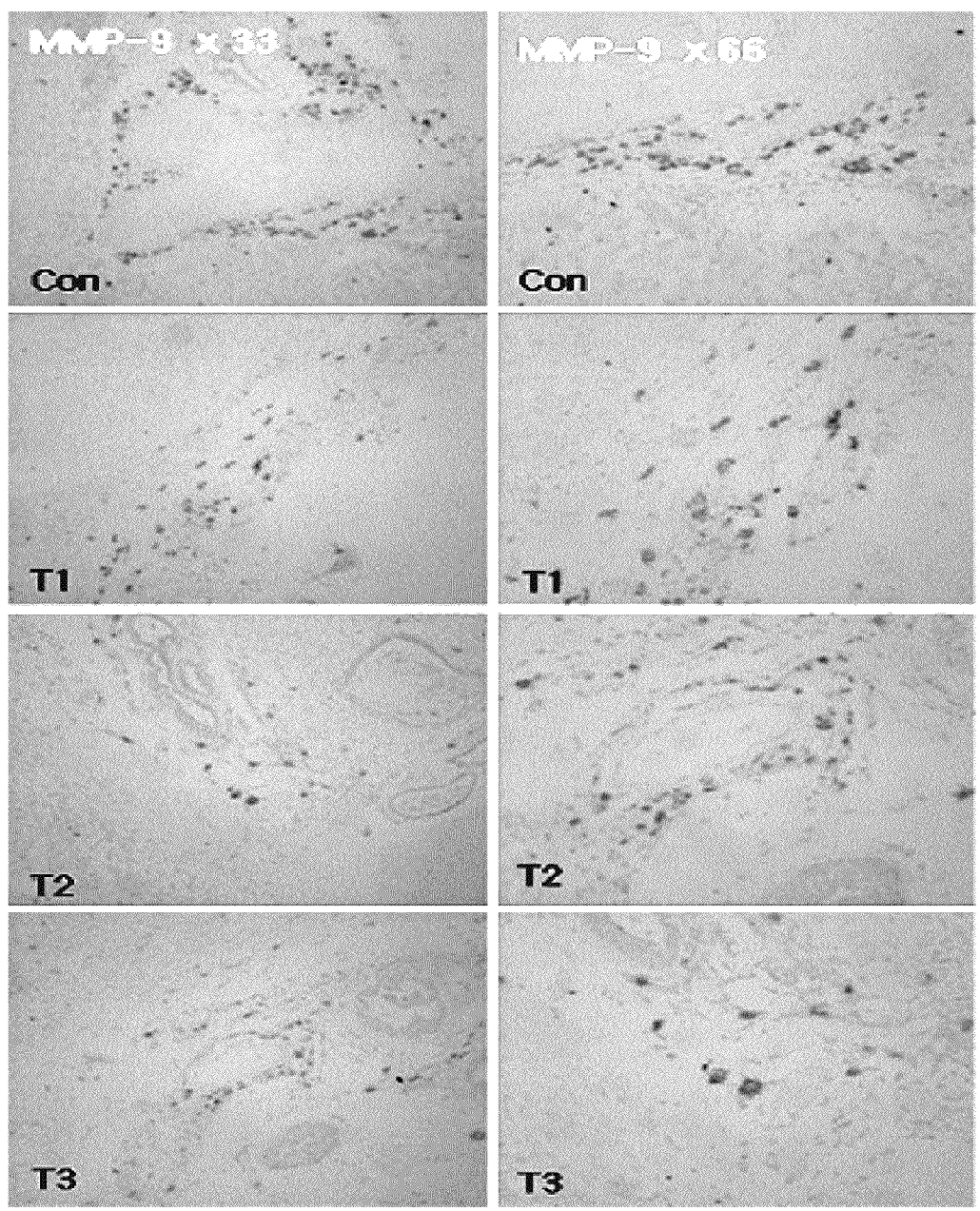
FIG. 4 is a set of photographs (x33 and x66) illustrating the immunohistological changes of MMP-9 observed after administering arazyme to the nude mice transplanted with human lung adenocarcinoma cell line A549:
Control: orally administered with 0 mg/kg of arazyme;
T1: orally administered with 150 mg/kg of arazyme;
T2: orally administered with 300 mg/kg of arazyme; and
T3: orally administered with 600 mg/kg of arazyme.
Figure 5:
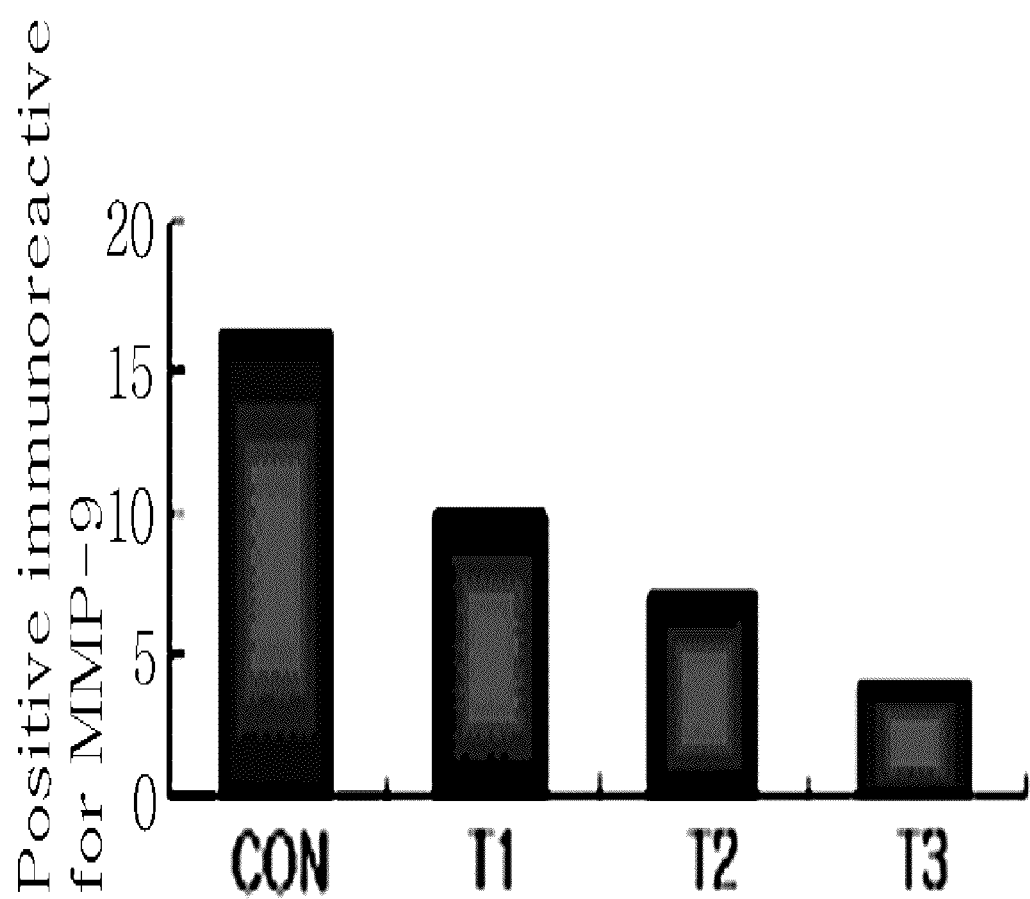
FIG. 5 is a graph showing the immunohistological expression level of MMP-9 observed after administering arazyme to the nude mice transplanted with human lung adenocarcinoma cell line A549:
Control: orally administered with 0 mg/kg of arazyme;
T1: orally administered with 150 mg/kg of arazyme;
T2: orally administered with 300 mg/kg of arazyme; and
T3: orally administered with 600 mg/kg of arazyme.

As a result, the expression of MMP-9 in the group treated with arazyme was reduced, compared with the control (FIGS. 4 and 5).

With the generation of MMPs (matrix metalloproteases), tumor cell infiltration and metastasis are also increased with inflammation in various cancer cases. That is carried out by MMP-9 and MMP-2 among many MMPs. In particular, growth factors including MAPKs, cytokines, and tumor promoters are involved in the higher signal transduction mechanism regulating the expression of MMP-9. So, the down-regulation of MMP-9 indicates the inhibition of tumor infiltration and metastasis.

Experimental Example 5

Effect of Arazyme on the Expression of NF-κB

Immunohistological observation on NF-κB was performed by the same procedure as described in Experimental Example 4. The primary antibody herein was anti-rabbit primary antibody NF-κB (1:200, Cell Signaling Technology Inc, USA) instead of MMP-9.

Figure 6:
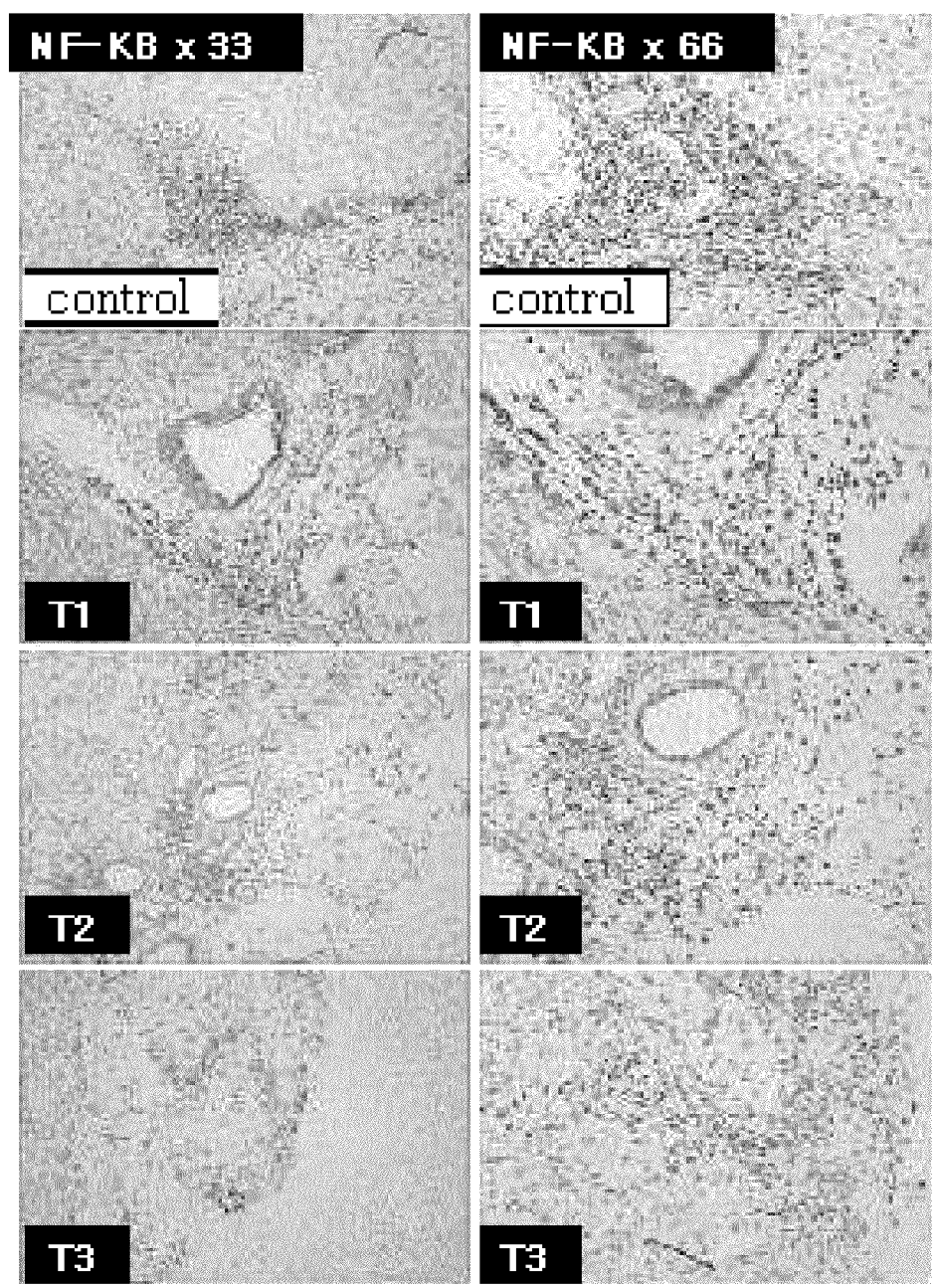
FIG. 6 is a set of photographs (x33 and x66) illustrating the immunohistological changes of NF-κB observed after administering arazyme to the nude mice transplanted with human lung adenocarcinoma cell line A549:
Control: orally administered with 0 mg/kg of arazyme;
T1: orally administered with 150 mg/kg of arazyme;
T2: orally administered with 300 mg/kg of arazyme; and
T3: orally administered with 600 mg/kg of arazyme.
Figure 7:
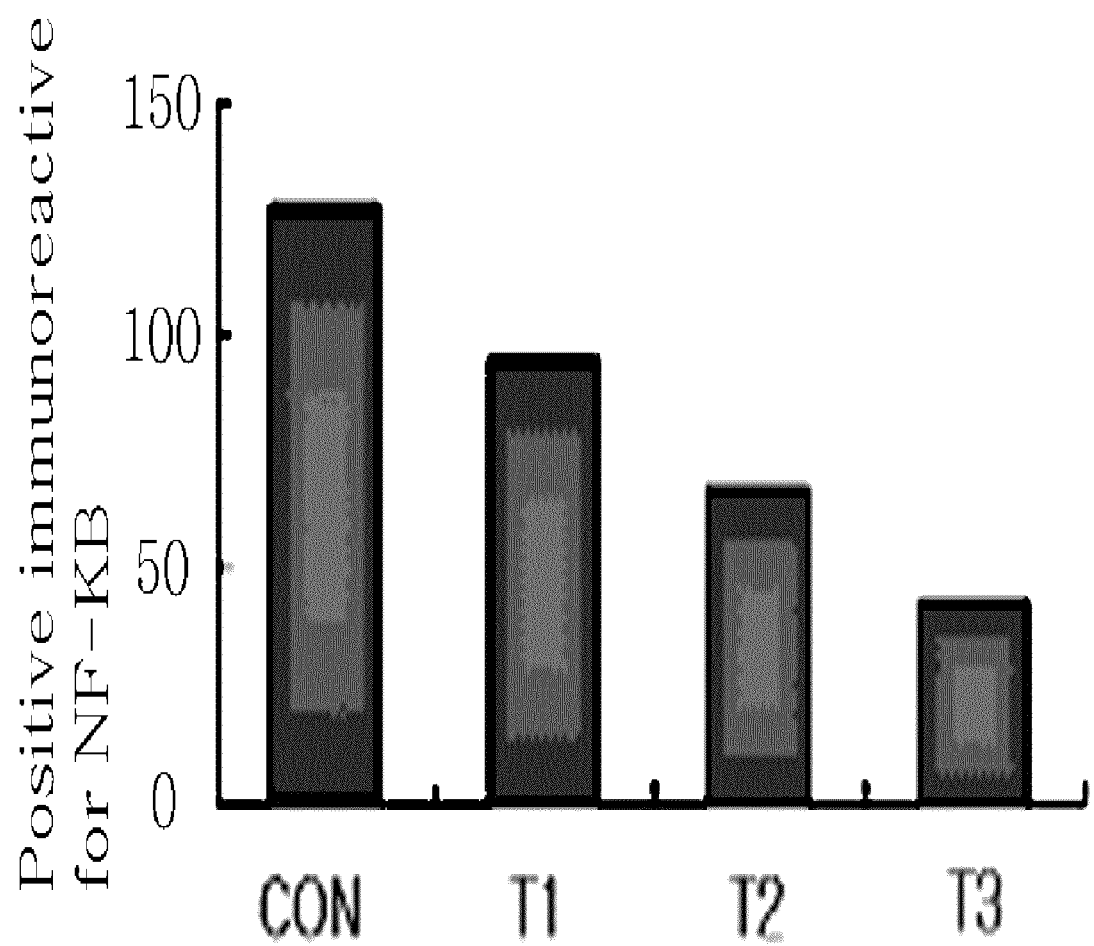
FIG. 7 is a graph showing the immunohistological expression level of NF-κB observed after administering arazyme to the nude mice transplanted with human lung adenocarcinoma cell line A549:
Control: orally administered with 0 mg/kg of arazyme;
T1: orally administered with 150 mg/kg of arazyme;
T2: orally administered with 300 mg/kg of arazyme; and
T3: orally administered with 600 mg/kg of arazyme.

As a result, the expression of NF-κB was reduced in the group treated with arazyme, compared with the control (FIGS. 6 and 7).

NF-κB is a transcription factor inducer activated by various environmental factors. It is also an important factor involved in drug refractoriness. It plays an important role in cytokine synthesis. When it is activated as a transcription factor inducing expressions of various genes involved in immune response or inflammation, it migrates to nucleus and increases the expression of inflammation related gene. So, the down-regulation of NF-κB indicates the inhibition of cancer.

Experimental Example 6

Effect of Arazyme on the Expression of PCNA

Immunohistological observation on PCNA was performed by the same procedure as described in Experimental Example 5. The primary antibody herein was anti-mouse primary antibody PCNA (1:800, Santa Cruz Bio, USA) instead of MMP-9.

Figure 8:
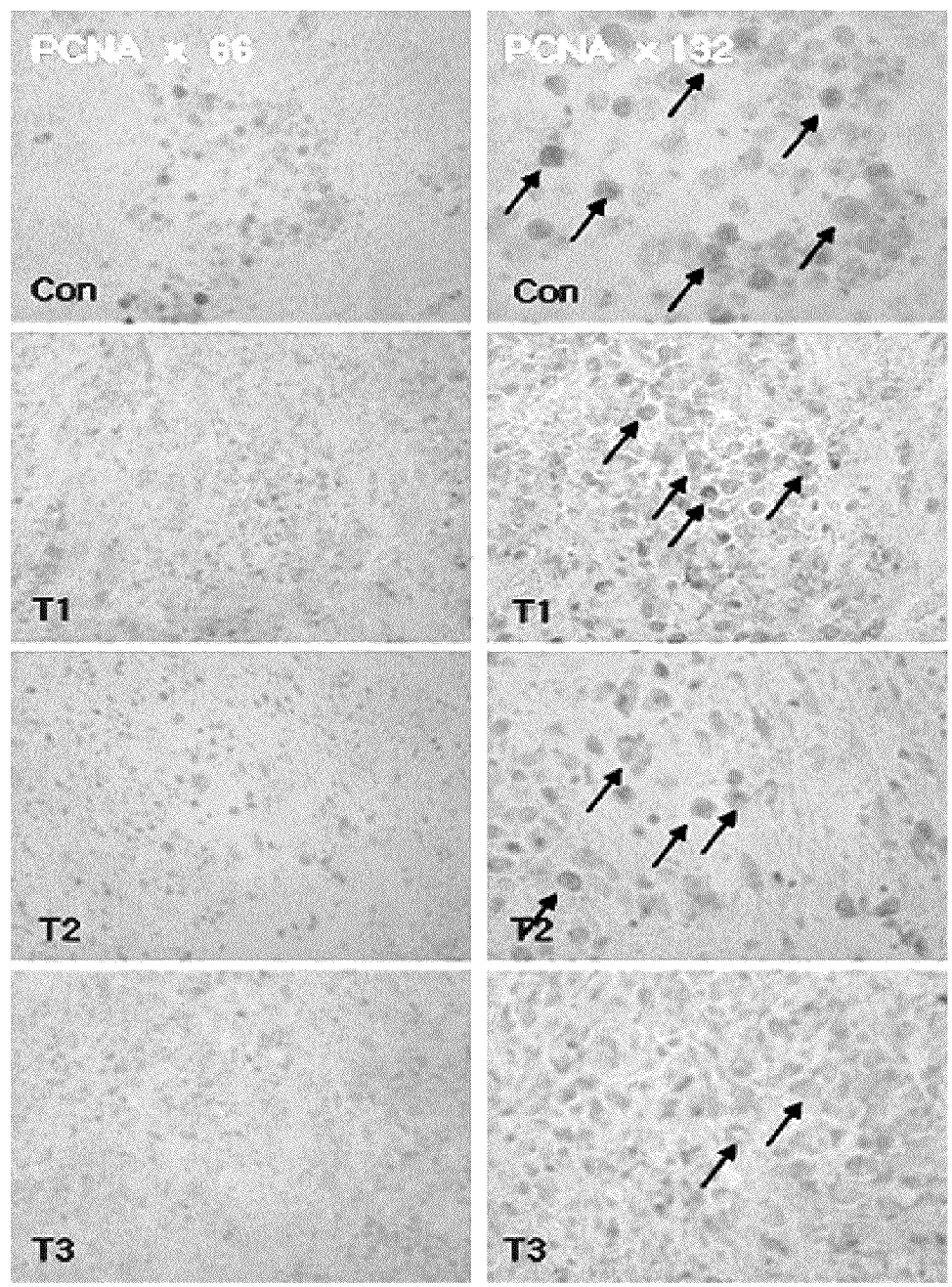
FIG. 8 is a set of photographs (x66 and x132) illustrating the immunohistological changes of PCNA observed after administering arazyme to the nude mice transplanted with human lung adenocarcinoma cell line A549:
Control: orally administered with 0 mg/kg of arazyme;
T1: orally administered with 150 mg/kg of arazyme;
T2: orally administered with 300 mg/kg of arazyme; and
T3: orally administered with 600 mg/kg of arazyme.
Figure 9:
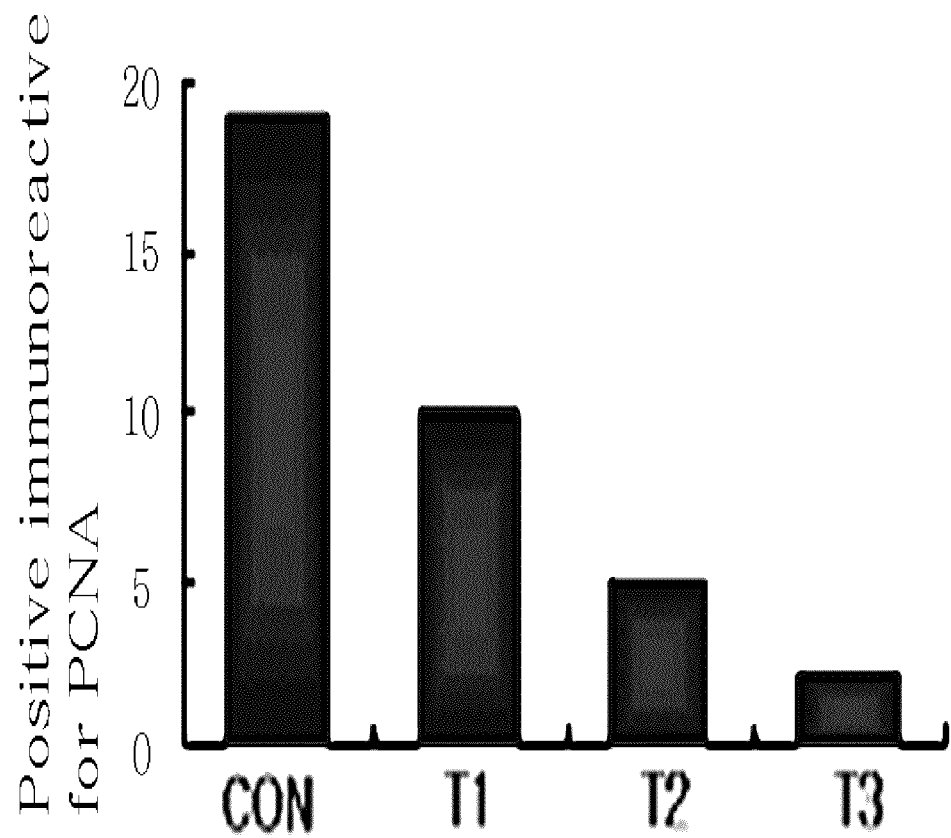
FIG. 9 is a graph showing the immunohistological expression level of PCNA observed after administering arazyme to the nude mice transplanted with human lung adenocarcinoma cell line A549:
Control: orally administered with 0 mg/kg of arazyme;
T1: orally administered with 150 mg/kg of arazyme;
T2: orally administered with 300 mg/kg of arazyme; and
T3: orally administered with 600 mg/kg of arazyme.
Figure 10:
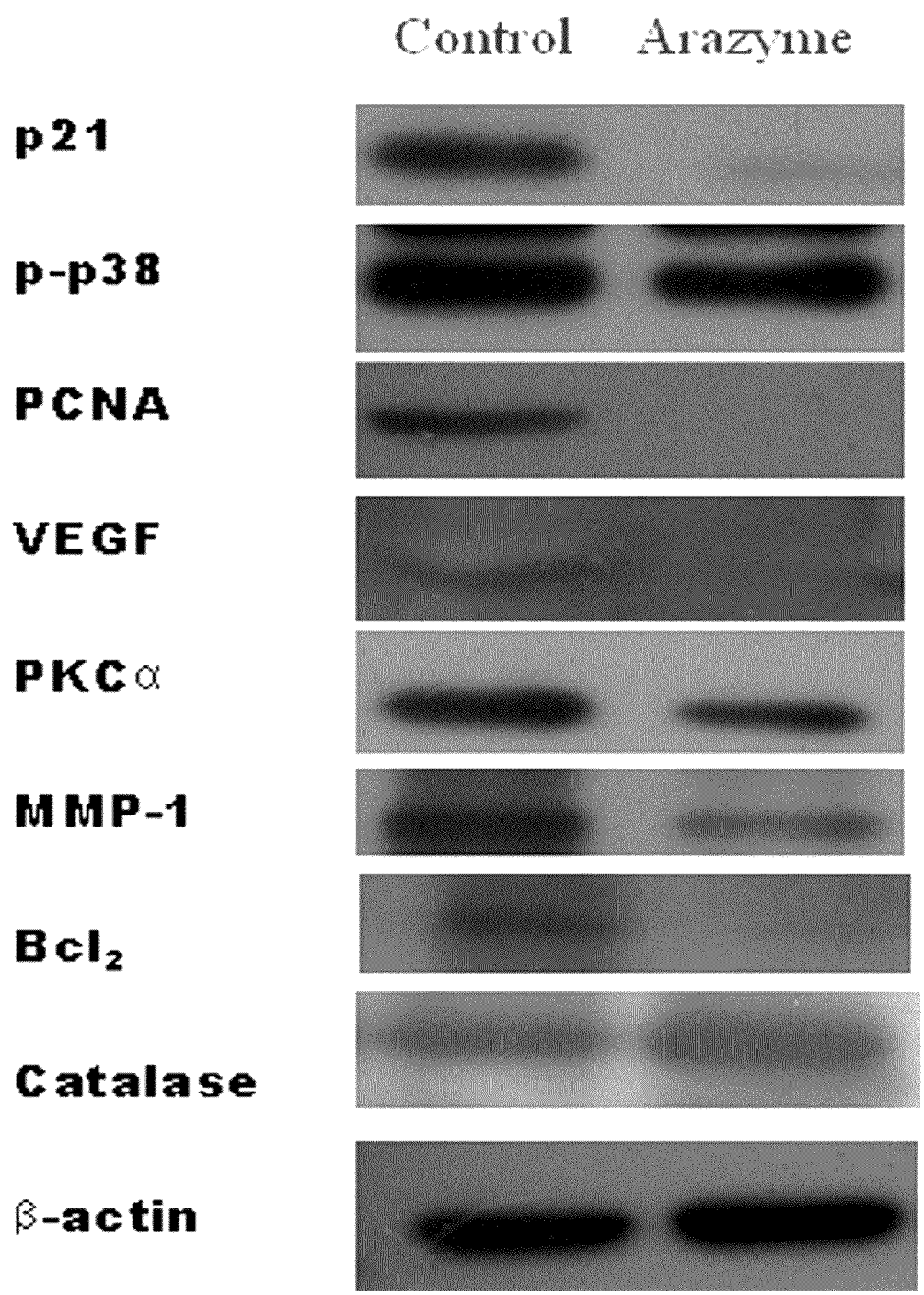
FIG. 10 is a diagram illustrating the results of immunoblotting examining the changes of expression of the protein involved in the growth, differentiation, proliferation and metastasis of tumor cells in human breast cancer cell line (MDA-MB-231) treated with arazyme (60 μg/ml).
Figure 11:
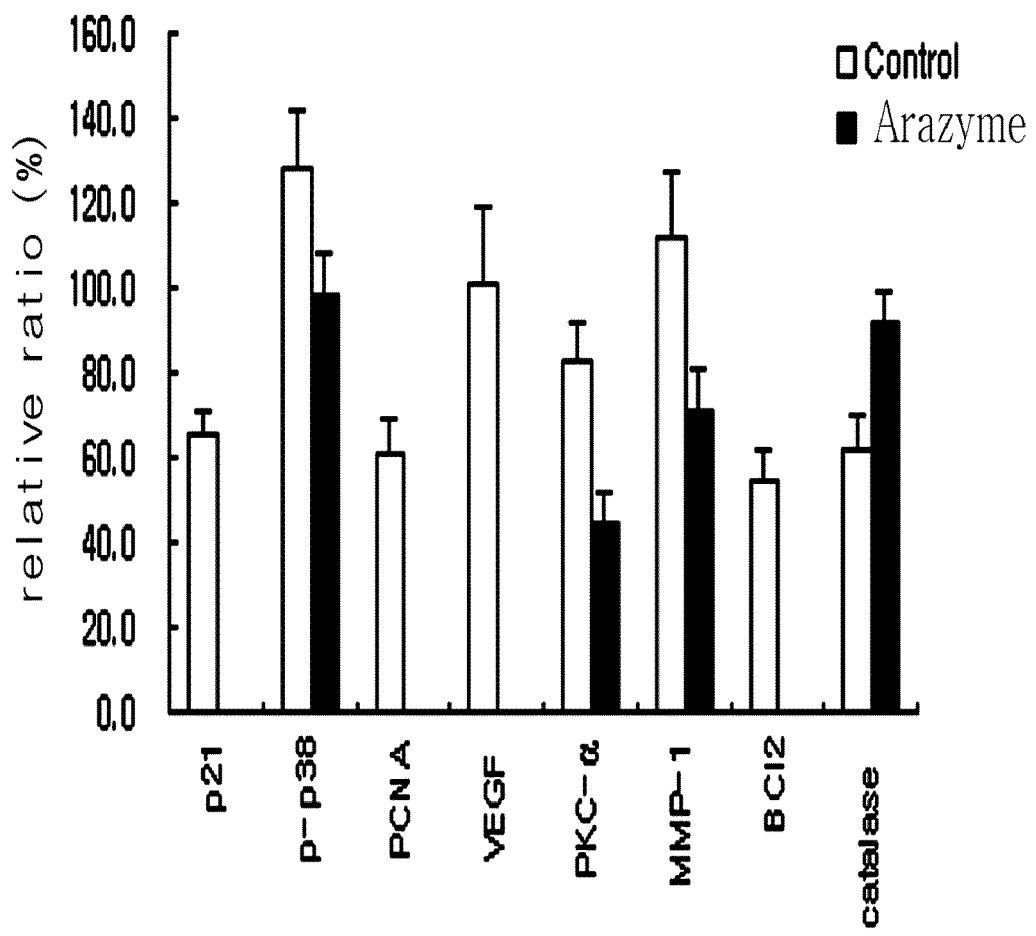
FIG. 11 is a graph illustrating the changes of expression of the protein involved in the growth, differentiation, proliferation and metastasis of tumor cells in human breast cancer cell line (MDA-MB-231) treated with arazyme (60 μg/ml, which are presented by comparative ratio.

As a result, the expression of PCNA was reduced in the group treated with arazyme, compared with the control (FIGS. 8 and 9).

PCNA is a coprotein of DNA polymerase delta. The expression of PCNA is known to be associated with the proliferation of keratinocytes, gliosis, stained skin lesion, and histopathological grade of non small cell lung carcinoma. Therefore, histoimmunofluorescence with PCNA has been an important index telling what region and how many are involved in tumor growth.

Experimental Example 7

Effect of Arazyme on the Expression of Human Breast Cancer Cell Protein

Immunoblotting was performed to investigate the expressions of proteins involved in tumor development using human breast cancer cells (MDA-MB-231) treated with arazyme in Example 3. MDA-MB-231 cells treated with arazyme (60 μg/ml) were suspended in RIPA buffer containing protease inhibitor cocktail tablet (Roche, Germany) and 0.1 mM sodium orthovandate ($Na_3VO_4$), followed by centrifugation at 4° C. with 14,000 rpm for 20 minutes to separate supernatant. The concentration of recovered cytoplasmic protein was measured by Bradford method (Bradford M M. *Anal. Biochem.* 1977; 72: 248-254) and each protein sample (80 g/well) proceeded to electrophoresis on 8~12% SDS-polyacrylamide gel, followed by electro-transfer onto PVDF membrane (Schleicher & Chuell, Dassel, Germany). Coomassie blue staining was performed to confirm if equal amount of protein was loaded. The protein was blocked in blocking solution containing 3% bovine serum albumin for one hour, followed by reaction with the primary antibodies p-21 (Santa Cruz Biotechnology Inc, USA) and β-Actin (1:500 Santa Cruz Biotechnology Inc, USA). Then, the protein was washed with TBS buffer containing 0.5% tween 200 thoroughly and then reacted with the secondary antibody anti-goat-HRP-antibody (1:1,000~1:2,000, Santa Cruz Biotechnology Inc, USA) corresponding to the primary antibody at room temperature for one hour. After washing with TBS buffer completely, the protein was reacted with chemiluminescence substrate (Super signal West Dura Extended Duration Substrate, PIERCE, USA) and exposed on medical X-ray film (Kodak, Japan) to detect the specific reaction. In addition to p-21, p-p38, PCNA (proliferating cell nuclear antigen), VEGF (vascular endothelial growth factor), BCl2, MMP-1 (matrix metalloproteinase 1) and catalase were used as the primary antibody. All the antibodies were provided from Santa Cruz Biotechnology Inc, USA. The secondary antibodies that corresponded to the above primary antibodies were selected. The secondary antibody corresponding to p-p38 was anti-rabbit-HRP-antibody, the secondary antibody corresponding to PCNA was anti-goat-HRP-antibody, the secondary antibody corresponding to VEGF was anti-goat-HRP antibody, the secondary antibody corresponding to BCl2 was anti-rabbit-HRP-antibody, the secondary antibody corresponding to MMP-1 was anti-mouse-HRP-antibody, and the secondary antibody corresponding to catalase was anti-goat-HRP-antibody. All the antibodies were provided from Santa Cruz Biotechnology Inc, USA.

As a result, the treatment of arazyme (60 μg/ml) to human breast cancer cells (MDA-MB-231) brought the significant down-regulations of p21, PCNA, VEGF and BCl2. The expressions of p-p38, PKC and MMP-1 were also reduced, compared with the non-treated control. On the contrary, the expression of catalase was increased in the group treated with arazyme (FIG. 1).

The tumor growth, differentiation, proliferation and metastasis in human breast cancer cells (MDA-MB-231) treated with arazyme (60 μg/ml) were measured and presented as relative ratios (FIG. 2). The results are shown in FIG. 1.

Experimental Example 8

Acute Toxicity of Arazyme

The following experiments were performed to see if arazyme of the present invention had acute toxicity in rats.

9-week old specific pathogen (SPF) free Wistar line female rats (Orient, Korea) were used in this experiment. The mice were divided into 4 groups, 4 rats per group, and raised in an animal laboratory at 22±3° C., with the humidity of 55±10%, and under the light condition of 12 L/12 D. The rats were inspected and adapted for 7 days in an animal laboratory. During the whole experimental period, the rats were accommodated less than 5 per each polycarbonate cage [240 W×390 L×175 H (mm)]. For individual identification, both skin mark using an oil marker and distinction cards were used. Solid feed for test animals (PMI Nutrition International, USA) was sterilized and provided freely. Tap water was given by a water bottle freely.

Arazyme was dissolved in sterilized injectable solution at different concentrations of 0, 1250, 2500 and 5000 mg/kg. The arazyme solution was orally administered to the rats (10 ml/kg) by using zonde once. After 1 week of adaptation, the rats were divided into 4 groups and arazyme was administered at different concentrations to those 10 week old rats. 24 hours later, autopsy was performed to investigate the toxicity of arazyme to each organ.

To evaluate the toxicity and observe general symptoms in the female rats according to the oral-administration of arazyme, behaviors, appearances and functions of the rats were investigated.

As a result, no abnormal symptoms in activity, walking, temperament and convulsion were observed in those animals after the administration of arazyme. Besides, no abnormal changes were observed in outward appearance including skin and hair, eyeball area, ears, reproductive organ, limbs, tail and in such functions as respiration, salivation, feces, vomiting, etc. From the investigation by anatomy 24 hours later, it was also confirmed that no abnormal symptoms were caused by arazyme in every organ. Estimated $LD_{50}$ of arazyme was at least 5000 mg/kg. No pathological symptoms were observed in liver, heart, lung and pancreas under microscope.

The Manufacturing Examples of the composition of the present invention are described hereinafter.

Manufacturing Example 1

Preparation of Pharmaceutical Formulations

<1-1> Preparation of Powders

| | |
|---|---|
| Arazyme | 2 g |
| Lactose | 1 g |

Powders were prepared by mixing all the above components, which were filled in airtight packs according to the conventional method for preparing powders.

<1-2> Preparation of Tablets

| | |
|---|---|
| Arazyme | 100 mg |
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| | |
|---|---|
| Arazyme | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<1-4> Preparation of Pills

| | |
|---|---|
| Arazyme | 1 g |
| Lactose | 1.5 g |
| Glycerin | 1 g |
| Xylitol | 0.5 g |

Pills were prepared by mixing all the above components according to the conventional method for preparing pills. Each pill contained 4 g of the mixture.

<1-5> Preparation of Granules

| | |
|---|---|
| Arazyme | 150 mg |
| Soybean extract | 50 mg |
| Glucose | 200 mg |
| Starch | 600 mg |

All the above components were mixed, to which 100 mg of 30% ethanol was added. The mixture was dried at 60° C. and the prepared granules were filled in packs.

<1-6> Preparation of Injectable Solutions

| | |
|---|---|
| Arazyme | 10 µg/ml |
| Weak HCl BP | until pH 7.6 |
| Injectable NaCl BP | up to 1 ml |

Arazyme was dissolved in proper volume of injectable NaCl BP. pH of the prepared solution was regulated as 7.6 by using weak HCl BP. The volume was adjusted by using injectable NaCl BP. The solution was well mixed and filled in 5 ml type I transparent glass ampoules. The ampoules were sealed by melting the glass of opening, followed by autoclave at 120° C. for at least 15 minutes for sterilization.

Manufacturing Example 2

Preparation of Food

The powders, tablets, capsules, pills and granules prepared in Manufacturing Example 1 can be applied to food. Foods containing the *Aranicola proteolycius* culture medium or arazyme were prepared as follows.

<2-1> Preparation of Flour Food 0.1~10.0 weight part of the *Aranicola proteolycius* culture medium or arazyme separated from the same was added to the flour. Health enhancing foods such as bread, cake, cookies, crackers and noodles were prepared with the flour mixture according to the conventional method.

<2-2> Preparation of Soups and Gravies 0.1~1.0 weight part of the *Aranicola proteolycius* culture medium or arazyme separated from the same was added to soups and gravies. Health enhancing meat products, soups and gravies were prepared with this mixture by the conventional method.

<2-3> Preparation of Ground Beef

Health enhancing ground beef was prepared by mixing 10 weight part of the *Aranicola proteolycius* culture medium or arazyme separated from the same with ground beef according to the conventional method.

<2-4> Preparation of Dairy Products 0.1~1.0 weight part of the *Aranicola proteolycius* culture medium or arazyme separated from the same was added to milk. Health enhancing dairy products such as butter and ice cream were prepared with the milk mixture according to the conventional method.

<2-5> Preparation of Sun-Sik

Brown rice, barley, glutinous rice and Yulmu (Job's tears) were gelatinized according to the conventional method, dried and pulverized to obtain 60-mesh powders.

Black soybean, black sesame and wild sesame were steamed and dried according to the conventional method and pulverized to obtain 60-mesh powders.

The *Aranicola proteolycius* culture medium or arazyme separated from the same was concentrated under reduced pressure, spray-dried and pulverized to obtain 60-mesh dry powders.

Sun-Sik was prepared by mixing the dry powders of the grains, seeds and the *Aranicola proteolycius* culture medium or arazyme separated from the same according to the below ratio.

Grains (brown rice: 30 weight part, Yulmu: 15 weight part, barley: 20 weight part, glutinous rice: 10 weight part), Seeds (wild sesame: 7 weight part, black soybean: 8 weight part, black sesame: 7 weight part), Dry powders of the *Aranicola proteolycius* culture medium or arazyme separated from the same (1 weight part),
*Ganoderma lucidum* (0.5 weight part),
*Rehmannia glutinosa* (0.5 weight part)

Manufacturing Example 3

Preparation of Beverages

Beverages containing the *Aranicola proteolycius* culture medium or arazyme separated from the same were prepared as follows.

<3-1> Preparation of Health Beverages

The *Aranicola proteolycius* culture medium or arazyme separated from the same (0.5 weight part) was mixed with liquid fructose (0.5 weight part), oligosaccharide (2 weight part), sugar (2 weight part), salt (0.5 weight part), and water (75 weight part). After mixing completely, the mixture was sterilized instantly and filled small containers such as glass bottles, pet bottles, etc, to prepare health beverages.

<3-2> Preparation of Vegetable Juice

Health enhancing vegetable juice was prepared by adding 0.5 g of the *Aranicola proteolycius* culture medium or arazyme separated from the same to 1,000 ml of tomato or carrot juice according to the conventional method.

<3-3> Preparation of Fruit Juice

Health enhancing fruit juice was prepared by adding 0.1 g of the *Aranicola proteolycius* culture medium or arazyme separated from the same to 1,000 ml of apple or grape juice according to the conventional method.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

---

We claim:

1. A method for treating lung cancer or breast cancer comprising administering a pharmaceutically effective dose of arazyme to a subject with lung cancer or breast cancer, wherein the arazyme is selected from the group consisting of:
   (a) a protein comprising the amino acid of SEQ ID NO:1; and
   (b) a protein encoded by a DNA comprising the nucleotide sequence of SEQ ID NO: 2.

2. The method of claim 1, wherein the arazyme is separated from *Aranicola proteolyticus* culture medium.

3. The method of claim 2, wherein the *Aranicola proteolyticus* is *Aranicola proteolyticus* HY-3 (Accession No: KCTC 0268BP).

4. The method of claim 1, wherein the arazyme inhibits the expression of MMP-9 (Matrix MetalloProteinase-9).

5. The method of claim 1, wherein the arazyme inhibits the expression of NF-κB (Nuclear Factor κB).

6. The method of claim 1, wherein the arazyme inhibits the expression of PCNA (Proliferating Cell Nuclear Antigen).

7. The method according to of claim 1, wherein the arazyme inhibits the expression of p21.

8. The method of claim 1, wherein the arazyme inhibits the expression of VEGF (Vascular Endothelial Growth Factor).

9. The method of claim 1, wherein the arazyme inhibits the expression of BCl2 (B-cell CLL/lymphoma 2).

10. The method of claim 1, wherein the arazyme inhibits the expression of p-p38.

11. The method of claim 1, wherein the arazyme inhibits the expression of PKC (Protein Kinase C).

12. The method of claim 1, wherein the arazyme inhibits the expression of MMP-1 (Matrix MetalloProteinase-1).

13. The method of claim 1, wherein the arazyme stimulates the expression of catalase.

* * * * *

SEQUENCE LISTING

```
<160> NUMBER OF SEQ ID NOS: 2

<210> SEQ ID NO 1
<211> LENGTH: 487
<212> TYPE: PRT
<213> ORGANISM: Aranicola proteolyticus
<220> FEATURE:
<221> NAME/KEY: BINDING
<222> LOCATION: (192)..(192)
<223> OTHER INFORMATION: Zn binding site
<220> FEATURE:
<221> NAME/KEY: BINDING
<222> LOCATION: (196)..(196)
<223> OTHER INFORMATION: Zn binding site
<220> FEATURE:
<221> NAME/KEY: BINDING
<222> LOCATION: (323)..(323)
<223> OTHER INFORMATION: Zn binding site

<400> SEQUENCE: 1

Met Gln Ser Thr Lys Lys Ala Ile Glu Ile Thr Glu Ser Ser Leu Ala
1               5                   10                  15

Ala Ala Ser Ser Ala Tyr Asn Ala Val Asp Asp Leu Leu His Tyr His
                20                  25                  30

Glu Arg Gly Asn Gly Ile Gln Val Asn Gly Lys Asp Ser Phe Ser Thr
            35                  40                  45

Glu Gln Ala Gly Leu Phe Ile Thr Arg Glu Asn Gln Thr Trp Asn Gly
    50                  55                  60

Tyr Lys Val Phe Gly Gln Pro Val Lys Leu Thr Phe Ser Phe Pro Asp
65                  70                  75                  80

Tyr Lys Phe Ser Ser Thr Asn Val Ala Gly Asp Thr Gly Leu Ser Lys
                85                  90                  95

Phe Ser Ala Glu Gln Gln Gln Ala Lys Leu Ser Leu Gln Ser Trp
            100                 105                 110

Ser Asp Val Ala Asn Ile Thr Phe Thr Glu Val Gly Ala Gly Gln Lys
        115                 120                 125

Ala Asn Ile Thr Phe Gly Asn Tyr Ser Gln Asp Arg Pro Gly His Tyr
    130                 135                 140

Asp Tyr Asp Thr Gln Ala Tyr Ala Phe Leu Pro Asn Thr Ile Tyr Gln
145                 150                 155                 160

Gly Gln Asn Leu Gly Gly Gln Thr Trp Tyr Asn Val Asn Gln Ser Asn
```

```
                    165                 170                 175
Val Lys His Pro Ala Ser Glu Asp Tyr Gly Arg Gln Thr Phe Thr His
                180                 185                 190
Glu Ile Gly His Ala Leu Gly Leu Ser His Pro Gly Asp Tyr Asn Ala
            195                 200                 205
Gly Glu Gly Asn Pro Thr Tyr Arg Asp Ala Ser Tyr Ala Glu Asp Thr
        210                 215                 220
Arg Glu Phe Ser Leu Met Ser Tyr Trp Ser Thr Asn Thr Gly Gly
225                 230                 235                 240
Asp Asn Gly Gly His Tyr Ala Ala Ala Pro Leu Leu Asp Asp Ile Ser
                245                 250                 255
Ala Ile Gln His Leu Tyr Gly Ala Asn Gln Thr Thr Arg Thr Gly Asp
            260                 265                 270
Thr Val Tyr Gly Phe Asn Ser Asn Thr Gly Arg Asp Phe Leu Ser Thr
        275                 280                 285
Thr Ser Asn Pro Gln Lys Val Ile Phe Ala Ala Trp Asp Ala Gly Gly
    290                 295                 300
Asn Asp Thr Phe Asp Phe Ser Gly Tyr Thr Ala Asn Gln Arg Ile Asn
305                 310                 315                 320
Leu Asn Glu Lys Ser Phe Ser Asp Val Gly Leu Lys Gly Asn Val
                325                 330                 335
Ser Ile Ala Ala Gly Val Thr Ile Glu Asn Ala Ile Gly Ser Gly
            340                 345                 350
Asn Asp Val Ile Val Gly Asn Ala Ala Asn Val Leu Lys Gly Gly
        355                 360                 365
Ala Gly Asn Asp Val Leu Phe Gly Gly Gly Ala Asp Glu Leu Trp
    370                 375                 380
Gly Gly Ala Gly Lys Asp Thr Phe Val Phe Ser Ala Val Ser Asp Ser
385                 390                 395                 400
Ala Pro Gly Ala Ser Asp Trp Ile Lys Asp Phe Gln Lys Gly Ile Asp
                405                 410                 415
Lys Ile Asp Leu Ser Phe Phe Asn Gln Gly Ala Gln Gly Gly Asp Gln
            420                 425                 430
Ile His Phe Val Asp His Phe Ser Gly Ala Gly Glu Ala Leu Leu
        435                 440                 445
Ser Tyr Asn Ala Ser Asn Asn Val Ser Asp Leu Ala Leu Asn Ile Gly
    450                 455                 460
Gly His Gln Ala Pro Asp Ile Leu Val Lys Ile Val Gly Gln Val Asp
465                 470                 475                 480
Val Ala Thr Asp Phe Ile Val
                485

<210> SEQ ID NO 2
<211> LENGTH: 2481
<212> TYPE: DNA
<213> ORGANISM: Aranicola proteolyticus
<220> FEATURE:
<221> NAME/KEY: misc_feature
<222> LOCATION: (402)..(402)
<223> OTHER INFORMATION: n is a, c, g, or t

<400> SEQUENCE: 2
cgagcgcgaa agacccggaa ggcacgaggt gattagtcaa aaaagaaaaa tgttattcct      60
gcgggaacta aaagtaccg gcggctaata ataaagagtt attaatctat aacgctttag     120
ccaaatttaa cttttagccg tctaaatccc agcacgattc gcttggctct gcaggccgca     180
```

```
tttttgttgg agtttgttac caactcatgg catttaagtt tcattaatat tgtaaataat    240
gcaaaaaacc agcataaatc cccttcgtaa cgataataaa tggctgatta ttttatgtgc    300
agttttacac cgctgcctat aattggaatc gattaccatt tatggtggta atcttatttg    360
ctgatatata tgcattaatt ctctctaaca cactgccggt ancggcgcat aaactccttc    420
ccgtaagcgt gcggttcgtt ctccgtggct tcctggcagg ttatgtctat ctgtctgatt    480
gaaaccaatc agctaatgag tggaatcgaa ccaatgcaat ctactaaaaa ggcaattgaa    540
attactgaat ccagccttgc ggctgcgagc tccgcttaca atgcagtaga tgatttgctg    600
cattatcatg agcgaggcaa cgggattcag gttaatggca aggactcatt ttctaccgaa    660
caagccgggc tgtttattac ccgcgagaac caaacctgga acggttataa agttttggc    720 caaccggtta aattaacgtt ctctttcccg gattataaat tctcttccac caacgtcgcc    780
ggcgataccg gactgagcaa attcagcgcg aacagcagc agcaggctaa gctgtcgctg    840
cagtcctggt ctgacgtggc caatatcacc tttaccgaag ttggtgccgg ccagaaggcc    900
aatatcacct tcggtaacta cagccaggat cgtcccggcc attatgacta cgatacccag    960
gcttacgcct tcctgccgaa caccatttat cagggccaaa acctgggcgg gcagacttgg   1020
tacaacgtca accagtccaa cgtgaaacat ccggccagcg aagactacgg ccgccagacc   1080
tttacccacg agattggcca tgcgttgggc ttgagccatc cggcgatta caacgccggc   1140 gaaggcaacc cgacttacag agatgccagc tacgccgaag atactcgtga gttcagcctg   1200
atgagttact ggagcgaaac caacaccggt ggcgacaacg gcgggcacta cgctgcggcg   1260
ccactgctgg atgacatttc cgctattcag catctgtatg gtgccaacca gaccacccgt   1320
accggcgata ccgtgtatgg cttcaactca aataccggac gtgacttcct cagtaccacc   1380
agcaatccgc aaaaagtgat ctttgcggcc tgggatgcgg gtggtaatga caccttcgat   1440
ttctccggtt acaccgctaa ccagcgtatt aatctgaacg agaaatcttt ctccgacgtg   1500
ggtgggctga aaggcaacgt gtccattgcc gcaggtgtga ccatcgagaa cgcgattggc   1560
ggttcaggca atgacgtgat cgtcggcaat gcggccaaca acgtgctgaa aggtggcgcg   1620
ggcaacgacg tgctgttcgg cggtggtggg gctgatgagc tgtggggcgg tgcgggcaaa   1680
gacacctttg tcttctctgc ggtcagcgat tctgcgccgg gtgcctccga ctggatcaag   1740
gatttccaga aaggcatcga taaaatcgac ctgtcattct tcaatcaggg cgcgcagggt   1800
ggcgatcaga tccacttcgt cgatcatttc agtggcgcag cggcgaagc cttgctgtct   1860 tacaatgcgt cgaataacgt cagcgatctg ccctgaata tcggcggcca tcaggccccg   1920
gacatcctgg tgaagatcgt cggccaggtt gatgtcgcca ctgactttat cgtttaacag   1980
tgcaggtgct aacgcccggc gccggttggc cgggcgttat acaggagacg atatgaaggg   2040
cagcttagcg cacgccgcct tagtggcagg cggcatgatg gttacggggg cagttatggc   2100
cagcagtttg gttcttccca gcgcgcaatc attggcgggg caatggctgg tcgccaatgc   2160
cgaacaacaa tgtcagattg agttttttggc cggtgaacag agtgaaatca acggctactc   2220
attggttgat cggcagcact gtttggaaaa ggtgttaacc gccgaggtgg tcggttggcg   2280
ccctgcaccg gacggcatcg ctttgctgcg gcgcgatggc agtacgctgg cgttcttctc   2340
gcgcgatggc gatatttacc gcaaccagct tggcgcggat gacggactga cgctgaaagc   2400
gctggtataa caacagcggg ttcggcagtc gaacccgccc tgagcagcct tacagataca   2460
gcgaacgtac gatcaggaaa t                                             2481
```